US011344708B2

(12) United States Patent
Heuser et al.

(10) Patent No.: US 11,344,708 B2
(45) Date of Patent: May 31, 2022

(54) MICRONEEDLE SYSTEM FOR ADMINISTERING LIQUID FORMULATIONS

(71) Applicant: LTS LOHMANN THERAPIE-SYSTEME AG, Andernach (DE)

(72) Inventors: Karsten Heuser, Bad Breisig (DE); Heiko Spilgies, Koblenz (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 149 days.

(21) Appl. No.: 15/565,025

(22) PCT Filed: Apr. 7, 2016

(86) PCT No.: PCT/EP2016/057675
§ 371 (c)(1),
(2) Date: Oct. 6, 2017

(87) PCT Pub. No.: WO2016/162449
PCT Pub. Date: Oct. 13, 2016

(65) Prior Publication Data
US 2018/0099133 A1 Apr. 12, 2018

(30) Foreign Application Priority Data
Apr. 7, 2015 (EP) .................................. 15162636

(51) Int. Cl.
*A61M 37/00* (2006.01)
*A61B 17/20* (2006.01)

(52) U.S. Cl.
CPC ....... *A61M 37/0015* (2013.01); *A61B 17/205* (2013.01); *A61M 2037/003* (2013.01);
(Continued)

(58) Field of Classification Search
CPC .................. A61M 37/0015; A61B 17/205
See application file for complete search history.

(56) References Cited

U.S. PATENT DOCUMENTS

| 6,780,171 | B2 | 8/2004 | Gabel et al. |
| 9,913,970 | B2 | 3/2018 | Arami et al. |

(Continued)

FOREIGN PATENT DOCUMENTS

| DE | 60305901 T2 | 2/2007 |
| EP | 2937111 A1 | 10/2015 |

(Continued)

OTHER PUBLICATIONS

International Search Report for PCT/EP2016/057675 dated Jul. 19, 2016.

(Continued)

*Primary Examiner* — Nathan R Price
*Assistant Examiner* — Weng Lee
(74) *Attorney, Agent, or Firm* — Faegre Drinker Biddle & Reath LLP

(57) ABSTRACT

The present invention relates to a microneedle system (MNS) for intradermally delivering solutions or formulations. The invention relates to a microneedle system, comprising a cover element (1), an active substance container (2), a frame (3), a microneedle array (MNA) (4) and a base plate (5), wherein the microneedle array (MNA) (4) is connected to the frame (3), and the base plate (5) has an opening for receiving the microneedle array (4), the cover element (1) and the base plate (5) are movably connected to one another, the base plate (5) is joined to a surgical tape (6), and the frame (3) and the base plate (5) can be linearly displaced with respect to one another.
The MNS according to the invention is suitable for intradermally administering medicinal drugs, active substances, pharmaceutical or cosmetic compositions or other substances to an individual, and preferably to a patient, over an extended period.

18 Claims, 3 Drawing Sheets

(52) U.S. Cl.
CPC ........... *A61M 2037/0023* (2013.01); *A61M 2037/0053* (2013.01); *A61M 2037/0061* (2013.01)

(56) References Cited

U.S. PATENT DOCUMENTS

| | | | |
|---|---|---|---|
| 10,046,152 B2 | 8/2018 | Sumida et al. | |
| 2003/0187395 A1 | 10/2003 | Gabel et al. | |
| 2009/0093772 A1* | 4/2009 | Genosar | A61M 5/14244 604/246 |
| 2010/0179473 A1* | 7/2010 | Genosar | A61M 5/14248 604/70 |
| 2011/0105952 A1* | 5/2011 | Bernstein | A61B 5/15105 600/573 |
| 2011/0172609 A1* | 7/2011 | Moga | A61M 5/14248 604/272 |
| 2011/0276027 A1 | 11/2011 | Trautman et al. | |
| 2012/0109065 A1 | 5/2012 | Backes | |
| 2014/0257190 A1* | 9/2014 | Yue | A61M 5/283 604/173 |

FOREIGN PATENT DOCUMENTS

| | | |
|---|---|---|
| WO | WO-0205889 A1 | 1/2002 |
| WO | WO-2014059104 A1 | 4/2014 |
| WO | WO-2014061339 A1 | 4/2014 |
| WO | WO-2014097837 A1 | 6/2014 |

OTHER PUBLICATIONS

Written Opinion of the International Searching Authority for PCT/EP2016/057675 dated Jul. 19, 2016 (in German).

\* cited by examiner ized pump, for example, implements the pushing out of the active substance container.

MICRONEEDLE SYSTEM FOR ADMINISTERING LIQUID FORMULATIONS

CROSS-REFERENCE TO RELATED APPLICATIONS

This application is a national stage application (under 35 U.S.C. § 371) of PCT/EP2016/057675 filed Apr. 7, 2016, which claims benefit of European Application No. 15162636.3, filed Apr. 7, 2015, both of which are incorporated herein by reference in their entirety.

The present invention relates to a microneedle system (abbreviated as MNS) for intradermally delivering solutions or formulations. The invention relates to a microneedle system, comprising a cover element (1), an active substance container (2), a frame (3), a microneedle array (abbreviated as MNA) (4) and a base plate (5), wherein the microneedle array (MNA) (4) is connected to the frame (3), and the base plate (5) has an opening for receiving the microneedle array (4), the cover element (1) and the base plate (5) are movably connected to one another, the base plate (5) is joined to a surgical tape (6), and the frame (3) and the base plate (5) can be linearly displaced with respect to one another.

The MNS according to the invention is suitable for intradermally administering medicinal drugs, active substances, pharmaceutical or cosmetic compositions or other substances to an individual, and preferably to a patient, over an extended period.

BACKGROUND OF THE INVENTION

Microneedle systems and devices in which microneedle arrays are used for the painless intradermal administration of medicinal drugs are known from the prior art.

The skin consists of several layers. The outermost layer of the skin, this being the stratum corneum, has known blocking properties to prevent foreign substances from penetrating into the body and the body's own substances from exiting the body. The stratum corneum, which is a complex structure composed of compacted horny cell residues having a thickness of approximately 10 to 30 micrometers, forms a watertight membrane for this purpose to protect the body. The natural impermeability of the stratum corneum prevents most pharmaceutical agents and other substances from being administered through the skin as part of an intradermal delivery.

As a result, various substances are therefore administered, for example, by generating micropores or cuts in the stratum corneum and feeding or delivering a medicinal drug into or beneath the stratum corneum. In this way, it is also possible to administer a number of medicinal drugs subcutaneously or intradermally or intracutaneously, for example.

For use, microneedle systems (MNS) composed of a microneedle array (MNA) and possibly further components require an element that presses the microneedles (also referred to as skin penetration elements) of the array (MNA) against the delivery site on the skin so as to penetrate the stratum corneum and thereby establish a fluid channel between the external medicinal drug reservoir (such as a container) and the skin by way of the MNA. If a liquid formulation is selected for the medicinal drug, an element that opens the active substance container and, depending on the design, also pushes the medicinal drug out of the active substance container, is necessary in the MNS. Various embodiments are known for implementing the former element, which generally employ a mechanical energy store for opening the active substance container. A syringe integrated into the MNS or a miniaturized pump, for example, implements the pushing out of the active substance container.

A corresponding simple microneedle system is described in WO 02/05889 A1. This device comprises a housing including an inside active substance container in the form of a flexible bladder. The flexible bladder is positioned in a cavity in the housing. The cavity is covered by a cover member, which can be pressed downward so as to press the flexible bladder against a microneedle array situated on the bottom of the housing. This opens the active substance container, and the liquid contained in the flexible bladder flows to several microneedles.

DE 603 05 901 T2 discloses a device composed of a housing and a cartridge. The cartridge comprises the container for the active substance-containing solution and, in addition to the bottom wall, comprises a lower outside wall that is spaced apart from the bottom wall and includes an integrated needle array. The housing comprises a base part, a peripheral side wall, and a cover member, which can be pivoted between an open and a closed position and is connected to the base part by a hinge, snap fit, interference fit or friction fit. The microneedle system is assembled by positioning the cartridge in the housing, wherein the cartridge is aligned in a defined position in the housing by way of a notch. The microneedle system is positioned on the patient's skin surface in such a way that the needle array pierces the surface of the skin before the cover member of the housing is pivoted into the closed position. When the cover member is closed, the active substance container is pierced. The cover member of the housing comprises a spring to apply pressure to the cartridge and causes the active substance-containing solution to be dispensed when the cover member is closed. Furthermore, a wristband is necessary for fixation.

The devices and methods known from the prior art for intradermally delivering active substances are only successful to a limited degree.

The known microneedle systems have the disadvantage that they apply a force to the MNA only during the brief use (several seconds or less), and the MNA during the subsequent usage phase (several minutes to several days) tends to detach again from the skin. For many uses, however, it is necessary to ensure a lasting force fit with the skin during the delivery or over an extended period.

Many known microneedle systems moreover have the disadvantage that applicators are needed, which are not an integral part of the microneedle system, but must be provided as an additional separate unit. For the intradermal delivery, an embodiment that combines the MNS and delivery system in one unit is desirable, wherein the design of the overall system, and in particularly the height and the diameter, does not influence comfortable use or wearing of the MNS.

All known devices comprising active substance containers moreover consist of a combination of a microneedle array with a syringe, a pump or a spring for dispensing the active substance-containing solution. Due to the design, these devices are inconvenient to use and complex to produce. A need exists for devices that are easy to produce and use.

This object is achieved according to the invention by a microneedle system (MNS), comprising a cover element (1), an active substance container (2), a frame (3), a microneedle array (4), a base plate (5) and a surgical tape (6) according to claim 1 and the dependent claims.

Figure 1:
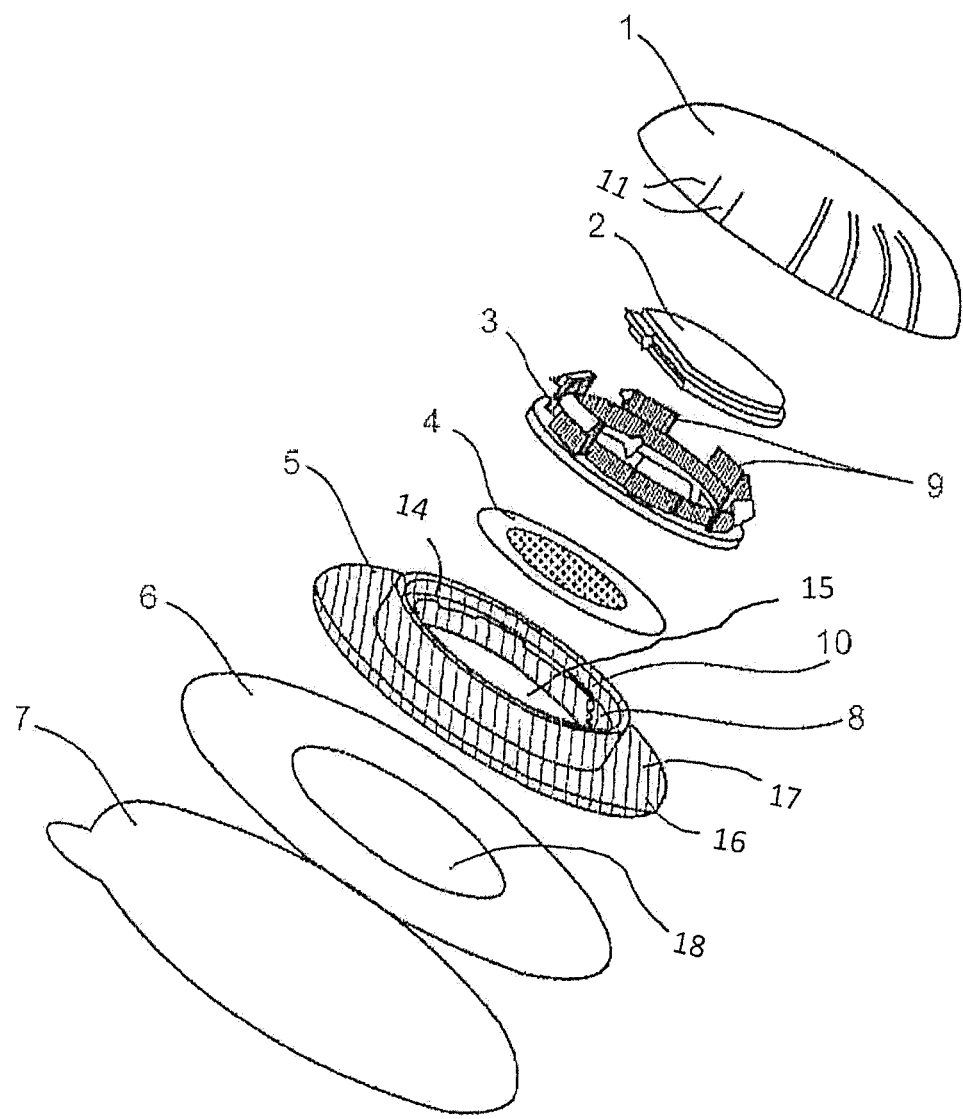
FIG. 1: shows an exploded view of the integral parts of the MNS according to the invention. In the illustrated exemplary embodiment, the overall system has a maximum diameter of 50 mm in terms of the surgical tape (6) and protective film (7) and a total height of approximately 7 mm.

In the MNS according to the invention, the microneedle array (4) is connected to the frame (3), preferably on the underside of the frame (3), and the base plate (5) has an opening for receiving the microneedle array (4).

The frame (3) can also be regarded as a mount for the microneedle array (4) and is used to fix the microneedle array (4) and to receive an active substance container (2).

The cover element (1) and the base plate (5) are movably connected to one another, preferably via a thread. The base plate (5) is furthermore entirely or partially joined to or provided with a surgical tape (6), and the frame (3) and the base plate (5) can be linearly displaced with respect to one another.

The MNS is preferably protected until use by a protective film (7), in particular on the surgical tape (6).

In contrast to the microneedle systems known from the prior art, the MNS according to the invention is thus substantially composed of an active substance container, which can be joined to the skin in one unit by way of a surgical tape. The MNS according to the invention does not require an additional applicator, no pump, syringe or spring. It is easy and cost-effective to produce. The MNS can, but does not have to, be supplemented with further integral parts. It is suitable for intradermally administering medicinal drugs, active substances, pharmaceutical or cosmetic compositions or other substances to an individual, and preferably to a patient, over an extended period. The MNS according to the invention is easy to handle and can be carried out directly by the individual at home or at the point of care, for example as part of self-medication by the patient or for cosmetic use. In particular, the piercing of the microneedles into the skin is a routine process and does not require checkups and monitoring by a physician or supervision by medical staff. This is in particular advantageous during extended or repeated deliveries since the patient or the individual does not require repeated care by the medical staff or over the extended period. This is possible since the needles of the MNA can be easily introduced into the stratum corneum, where they remain over an extended period, even without re-pressing, so that the delivery of the desired amount of medicinal product, active substance, pharmaceutical composition or other substances, including directly by the patient or the individual, is ensured by way of the MNS according to the invention.

The invention therefore relates to a microneedle system for intradermal delivery, comprising:

i.) a cover element (1) over an active substance container (2), wherein the active substance container (2) is accommodated in a frame (3) comprising a microneedle array (4); and ii.) a base plate (5), wherein the base plate (5) has an opening for receiving the microneedle array (4), and the cover element (1) and the base plate (5) are movably connected to one another;

iii.) the base plate (5) is entirely or partially joined to a surgical tape (6); and iv.) the frame (3) and the base plate (5) are movably connected to one another, wherein the frame (3) comprising a microneedle array (4) can be linearly displaced in the direction of the opening of the base plate (5).

Furthermore, the cover element (1) and the base plate (5) are preferably movably connected to one another via a thread.

According to the invention, the term "intradermal delivery" (synonym: "intracutaneous delivery") describes the administration of substances via the MNA into the skin and requires the microneedles to pierce the skin.

According to the invention, after fixation of the microneedle system on the skin by way of a surgical tape (6), in a first step the cover element (1) is rotated on the base plate (5) via the thread and, in this way, the frame (3) comprising a microneedle array (4) is moved in the direction of the opening of the base plate (5).

In the course of this movement or stroke, the frame (3) comprising a microneedle array (4) reaches the plane of the opening of the base plate (5), wherein the protruding microneedles penetrate into the skin. At the same time, the active substance container (2), which was entrained, reaches one or more opening elements (8) (mandrel or the like), so that the container breaks open, and the solution or formulation is dispensed, and more particularly into the provided MNA. The opening elements (8) are provided in such a way that the opening elements (8) make contact with and open the active substance container (2) as soon as the microneedle array (4) reaches the plane of the opening of the base plate (5) (referred to as the delivery position).

In a preferred embodiment of the invention, the frame (3) of the microneedle system comprises at least one or more catch hooks (9), which preferably protrude and can engage in the base plate (5). The base plate (5) can comprise appropriate recesses (10). The catch hooks (9) furthermore serve as engagement points for the stroke out of the above-mentioned rotational movement of the cover element (1) relate to the base plate (5).

The catch hooks (9) provide the frame (3) with a defined position with respect to the base plate (5) and also prevent a (full) rotation of the frame (3) or on the base plate (5). At the same time, the catch hooks are formed on the frame (3), and the recesses (10) are formed in the base plate (5), in such a way that the frame (3) is movably mounted in the base plate (5).

Once the frame (3) is situated in the plane of the base plate (5) or surgical tape (6), the MNA (4) is localized in the opening of the base plate (5).

The frame (3) and the base plate (5) are movably connected to one another, but can be linearly displaced with respect to one another, wherein the catch hook or hooks (9) is or are to prevent a rotational movement or a rotation of the frame (3) on the base plate (5).

In a particularly preferred embodiment of the microneedle system, the cover element (1) and the base plate (5) are movably connected to one another via a thread. In a preferred embodiment of the microneedle system, the active substance container is opened by a quarter turn of the thread. The preferred angle of rotation is 90°. Depending on the design, the angle of rotation can be between 10° and 350°. It may be indicated to the user when the maximum angle of rotation has been reached, which in the simplest case takes place, for example, by a position marking at the stop.

In a further preferred embodiment of the microneedle system, the surgical tape (6) is protected by a protective film (7).

In a further preferred embodiment of the microneedle system, the diameter of the microneedle system is at least 10 mm, preferably at least 25 mm, and particularly preferably at least 50 mm.

In a further preferred embodiment of the microneedle system, the height of the microneedle system is no more than 30 mm, preferably no more than 20 mm, and particularly preferably no more than 10 mm.

In a further preferred embodiment of the microneedle system, the active substance container (2) is a blow-fill-seal container or a disposable container.

In a further preferred embodiment of the microneedle system, the active substance container (2) contains one or more substances, medicinal drugs, active substances, solutions or (liquid) formulations, in particular pharmaceutical active agents or pharmaceutical compositions, in particular antibiotics, antiviral active agents, analgesic drugs, anesthetics, appetite suppressants, arthritis drugs, antidepressants, antihistamines, anti-inflammatory agents, antineoplastic agents, vaccines, including DNA vaccines, and the like, proteins, peptides or fragments thereof, nucleic acids or parts thereof, as well as cosmetics, nutritional supplements, sunscreens, insect repellents, radical scavengers, hydrating agents and dyes.

The active substance container (2) preferably contains solutions or (liquid) formulations comprising active agents or auxiliary agents.

The term "solution" or "(liquid) formulation" shall mean that one or more substances are involved, having at least such a state of aggregation that the substance can be intradermally delivered by the MNA (4) at room temperature within a predefined delivery period. Suitable viscosities are values between 0 and 200 mPa*s.

The invention likewise relates to a method for producing a microneedle system according to the invention, comprising the following steps:
  a) providing an active substance container (2), preferably produced by way of a blow-seal method;
  b) providing a microneedle array (4); and
  c) combining the active substance container (2) and the microneedle array (4) with the frame (3), the base plate (5) and the surgical tape (6) to form the microneedle system.

The invention also relates to a method for carrying out an intradermal delivery, comprising the following steps:
  a) fixing a microneedle system according to the invention to the skin by way of the surgical tape (6);
  b) transferring the microneedle system from a storage position (first position) into the delivery position (second position), for example by rotating the cover element (1) relative to the base plate (5).

A preferred embodiment of the invention relates to a method for carrying out an intradermal delivery, comprising the following steps:
  a) fixing a microneedle system, comprising:
    i.) a cover element (1) over an active substance container (2), wherein the active substance container (2) is accommodated in a frame (3) comprising a microneedle array (4); and
    ii.) a base plate (5), wherein the base plate (5) has an opening for receiving the microneedle array (4), and the cover element (1) and the base plate (5) are movably connected to one another;
    iii.) the base plate (5) is entirely or partially joined to a surgical tape (6); and
    iv.) the frame (3) and the base plate (5) are movably connected to one another, wherein the frame (3) comprising a microneedle array (4) can be linearly displaced in the direction of the opening of the base plate (5),
  to the skin by way of the surgical tape (6); and
  b) transferring the microneedle system from a storage position (first position) into the delivery position (second position), for example by rotating the cover element (1) relative to the base plate (5), wherein the active substance container (2) is opened by an opening element (8).

The invention also relates to a method for intradermal delivery, comprising the following steps:
  a) fixing a microneedle system according to the invention to the skin by way of the surgical tape (6);
  b) transferring the microneedle system according to the invention from a storage position into the delivery position, for example by turning the thread between the cover element (1) and the base plate (5); and
  c) delivering one or more substances into the selected region of the skin of an individual.

The invention furthermore relates to the preparation of one or more substances, medicinal drugs, active substances, solutions or (liquid) formulations for the intradermal delivery in a microneedle system according to the invention.

The MNS according to the invention can comprise one or more MNAs (4) and one or more active substance containers (2). The MNS according to the invention allows the stratum corneum to be pierced painlessly and the microneedles to penetrate into the skin with little force expenditure. The MNS according to the invention particularly advantageously enables a constant force fit with the skin, and allows a constant and lasting force fit between the skin and the MNA (4) to be maintained during the delivery. The MNS according to the invention is designed so as to first be applied to the skin during use and fixed. The MNA (4) is in a first position, this being the storage position. By rotating the cover element (1) about the base plate (5), the frame (3) is linearly displaced with respect to the base plate (5) (delivery mechanism). The MNA (4) is moved from the storage position into the delivery position, while the active substance container (2) is opened by an opening element (8). The solution contained in the active substance container (2) flows out of the active substance container (2) and into the MNA or into the microneedles. In the delivery position, the microneedles have pierced the stratum corneum and penetrated into the skin. The liquid is intradermally delivered through the microneedles. By actuating the delivery mechanism, constant tension is generated and maintained between the skin and the MNS. As a result, a lasting force fit exists between the MNS and the skin during the entire intradermal delivery, so that the solution can also be administered over an extended period. The MNA (4) remains in the skin during the entire delivery, without the needles of the MNA (4) detaching from the skin.

The cover element (1) has a shape and dimensions complementary to those of the base plate (5). The cover element (1) and the base plate (5) form a housing. The cover element (1) preferably comprises a thread for locking the cover element (1) in a closed position and for transferring the MNA from the storage position into the delivery position.

The cover element (1) has an upper side and a bottom side, wherein the bottom side is inwardly directed facing the base plate (5), and preferably is in contact with the catch hooks (9). The cover element (1) has the shape of a curved cap, for example. The upper side of the cover element (1) preferably has a structure that facilitates the transfer from the storage position into the delivery position. For example, the upper side of the cover element (1) has one or more grooves that prevent slipping. Furthermore, the cover element (1) can comprise one or more markings (11), which define how the MNS can be transferred from the storage position into the delivery position. The bottom side comprises a peripheral thread (12), which is complementary to the thread (13) of the base plate (5), so that the cover element (1) and the base plate (5) can be connected by turns of the thread. At the same time, the turning of the thread between the cover element (1) and the base plate (5) effectuates the transfer of the MNA from the storage position into the delivery position.

The cover element (1) and the base plate (5) form a housing, having an inside cavity suitable for accommodating the frame (3), the MNA (4) and the active substance container (2).

The base plate (5) has a peripheral projection (14), including an opening (15), which is inwardly offset with respect to the base plate edge (16). This projection serves as a spacer for generating the cavity. On the outer side (17) of the edge a thread (13) is provided, which is complementary to the thread (12) of the cover element (1). See FIG. 2 To create the cavity, the cover element (1) is placed on the base plate (5), and the thread is not turned. The cavity delimited by the cover element (1) and the base plate (5) is reduced by a partial or full turn of the thread, or by multiple turns of the thread.

In the storage position, the MNA (4) is located above the skin, and the microneedles have not penetrated into the stratum corneum. During the transition into the delivery position, the cavity is reduced, and the MNA (4) is lowered. In this process, the microneedles penetrate into the skin, and preferably into the stratum corneum or through the stratum corneum, and remain in this position for the duration of the delivery or the duration of the use of the MNS.

The frame (3) is dimensioned so as to be able to accommodate the active substance container (2). The active substance container (2) is preferably inserted or fixed in the frame (3) in such a way that it is likewise linearly displaced with respect to the base plate (5) during the turn of the thread.

The active substance container (2) is made of a material that can be opened by at least one opening element (8). In preferred embodiments of the invention, the active substance container (2) is produced by way of a blow-fill-seal process. Appropriate methods are known from the prior art and described, for example, in Andrew. W. Goll (ISPE (2012) Knowledge Brief, KB-0025-Jun12). Particularly preferred embodiments of the MNS according to the invention relate to those in which a blow-fill-seal container is used.

The MNS according to the invention furthermore comprises a surgical tape (6) for attaching the MNS to the skin. The term surgical tape (6) covers any attachment means suitable for attaching the MNS to the skin surface. For example, the surgical tape (6) can comprise a fixed carrier and a chemical or biological substance, and preferably an adhesive. The surgical tape (6) may also only comprise or consist of one or more chemical and/or biological substances, wherein the one or more chemical and/or biological substances are applied directly to the underside of the base plate (5) and are suitable for attaching the MNS to the skin surface. The surgical tape (6) may also comprise or consist of a structured surface, for example a nanostructure, which is suitable for attaching the MNS to the skin surface. The crucial aspect is that the surgical tape (6) generates appropriately strong attachment and fixation on the skin surface, so that a constant force fit is created between the skin and the MNA (4), and this force fit between the skin and the MNA (4) is maintained during the delivery. The selection of the suitable surgical tape (6) depends on the tightness of the skin in the particular region (for example the abdomen or back), the amount of fatty tissue in and beneath the stratum corneum in the particular region, the body mass index of the individual, the age of the individual, the eating habits of the individual (such as the intake of liquids), the lifestyle habits of the individual (such as the sun exposure of the particular skin region), and possibly other factors. Accordingly, a person skilled in the art can select respectively suitable surgical tapes (6) for different individuals or patients and/or skin regions. The selection of the surgical tape (6) furthermore depends on the size of the MNS and the materials used in the MNS and/or the weight of these materials. Examples of suitable surgical tapes (6) include customary commercially available (pressure-sensitive) adhesives on a carrier, and possibly also comprising double-sided coatings.

The surgical tape (6) is securely joined to the base plate (5). In a particular embodiment, the surgical tape (6) forms an integral part of the base plate (5). The surgical tape (6) has one or more recesses (18) through which the microneedles of the MNA (4) pass when the delivery position is being set and through which the microneedles project during the delivery. The recessed region of the surgical tape (6) may optionally be protected by a protective film (7) or the like until the delivery or until fixation on the skin.

According to the invention, the microneedle array (MNA) (4) (synonym: microneedle path or microneedle pad) carries one or more skin penetration elements. In some embodiments, the skin penetration elements are disposed in an array of rows and columns, which are spaced apart from one another by a substantially equal distance. The actual length and spacing of the skin penetrating elements may depend on the solution to be administered and the administration site on the body of the individual or patient. Typically, the skin penetration elements are needles, and preferably hollow needles, which are fixed on or to a carrier and protrude from this carrier. The skin penetrating elements are disposed in an array that is provided for administering an effective amount of a solution over a defined time period through the skin of an individual/a patient. Typically, the microneedle array (4) has a surface area of approximately 1 $cm^2$ to approximately 10 $cm^2$, and preferably of approximately 2 to 5 $cm^2$.

The skin penetration elements are preferably hollow needles, which each have an axial passage and a chamfered, pointed outer tip for piercing the skin of the individual/patient. The skin penetration elements are attached in holes in a fixed carrier in such a way that the solution is able to flow from the active substance container (2) through the axial passages of the hollow needles. The skin penetration elements can be attached in the openings of the fixed carrier by way of a suitable adhesive or interference fit. In an alternative embodiment, micro skin penetration elements may be designed in one piece with the fixed carrier. The skin penetration elements preferably each have one chamfered, tapered tip and one axial passage, so as to establish a fluid connection between the active substance container (2) and an intradermal site in the skin of the patient.

The skin penetration elements preferably have a length that is suitable for achieving the desired skin penetration depth. The length and the thickness of the skin penetration elements are selected based on the solution to be administered, the thickness of the skin, and the target region in which the MNS is provided. In embodiments of the invention, the skin penetration elements can be microneedles, microtubes, solid or hollow needles, lancets and the like. In a preferred embodiment, the skin penetration elements are hollow needles or cannulas made of stainless steel. The size of the needles is approximately 24 gauge to 50 gauge, and preferably approximately 30 gauge to approximately 36 gauge, and in the most preferred variant, the size is approximately 34 gauge. Smaller needles penetrate the skin surface more easily than large needles and are generally preferred. The needles are located in the MNS on the underside of the frame (3) so as to provide an effective length of approximately 50 micrometers to approximately 5000 micrometers. In another embodiment, the needles have an effective length of approximately 500 micrometers to approximately 3000 micrometers. In further embodiments, the needles can have an effective length in the range of approximately 1000 micrometers and 2000 micrometers. Typically, the needles have an effective length of approximately 500 micrometers to approximately 1000 micrometers.

The integral parts of the MNS, and in particular the cover element (1), the frame (3), the base plate (5), optionally the carrier material of the MNA (4) and/or optionally the carrier material of the surgical tape (6), can be made of a suitable plastic material. Typically, non-reactive, inert, well-tolerated, biocompatible, such as dermatologically tested, plastic material is used for this purpose. Suitable plastic materials include polyethylene, polypropylene, polyesters, polyamides, polycarbonates, and copolymers thereof.

In the MNA (4), the skin penetration elements form an array (which is to say an arrangement), for example in the form of rows and columns spaced apart from one another. One, at least 2, more, or a plurality of skin penetration elements may be provided in the MNA (4), for example 10 to 1,000,000, preferably 50 to 100,000, and particularly preferably 100 to 10,000 skin penetration elements. The MNA (4) can, for example, be produced from a silicon wafer, which is machined and etched so as to form the individual needles. In alternative embodiments, the MNA (4) can be produced from stainless steel, tungsten steel, and alloys of nickel, molybdenum, chromium, cobalt and titanium. In further embodiments, the MNA (4) can be produced from ceramic materials, glass, polymers, and other non-reactive materials.

The array of skin penetration elements is typically disposed in rows and columns; however, the skin penetration elements may be disposed in other suitable patterns. The skin penetration elements are preferably spaced sufficiently apart from one another, so that the skin penetration elements are able to penetrate the skin to a depth that is substantially uniform across the entire array, without interfering with one another. The preferred penetration depth of the needles is defined by the stratum corneum, which is preferably completely or substantially completely pierced. In preferred embodiments, the skin penetration elements penetrate into the skin to a uniform depth and/or pierce the skin so as to administer the solution at the selected skin depth, and reduce the risk of leakage during the administration of the substance. The number of skin penetration elements in the array may vary as a function of the dimensions of the skin penetration elements, the substance to be administered, and the penetration depth.

The MNS according to the invention can comprise one or more active substance containers (2). The active substance containers (2) can have differing volumes or be designed to be loaded with differing volumes of solution. The selection of the volume is dependent on the (active) substance to be administered, or the agent to be administered, the selected formulation, the dosage, the treatment regimen, and other factors. The delivery duration depends on the volume of the active substance container (2), the (active) substance to be administered, the selected formulation, the dosage, the treatment regimen, the selected MNA (4) (such as the inside diameter of the skin penetration elements), the properties of the skin in the particular region, and other factors. For example, the MNS is suitable for deliveries of 0.5 minute to 10 days, especially 5 minutes to 1 day, preferably 1 to 5 hours, and particularly preferably approximately 2 hours. During this time, the MNS according to the invention ensures a constant force fit between the skin and the MNA (4), without the needles having to be re-pressed.

One embodiment of the MNS according to the invention is illustrated by way of example by the following figures and examples.

EXAMPLE 1

Composition of an MNS According to FIG. 1

The active substance solution is located in a blow-fill-seal container (2), which is situated in a frame (3). The MNA (4) is connected to the underside of the frame (3). The frame (3) is movably mounted in a base plate (5), the frame (3) and the base plate (5) being linearly displaceable with respect to one another, and the catch hooks on the frame (3) defining the stroke and preventing a rotational movement. The base plate (5) is securely joined to the surgical tape (6) and protected until use by a protective film (7). The frame or cap (3) and the base plate (5) are movably connected via a thread.

EXAMPLE 2

Use of the Delivery Mechanism

Figure 2:
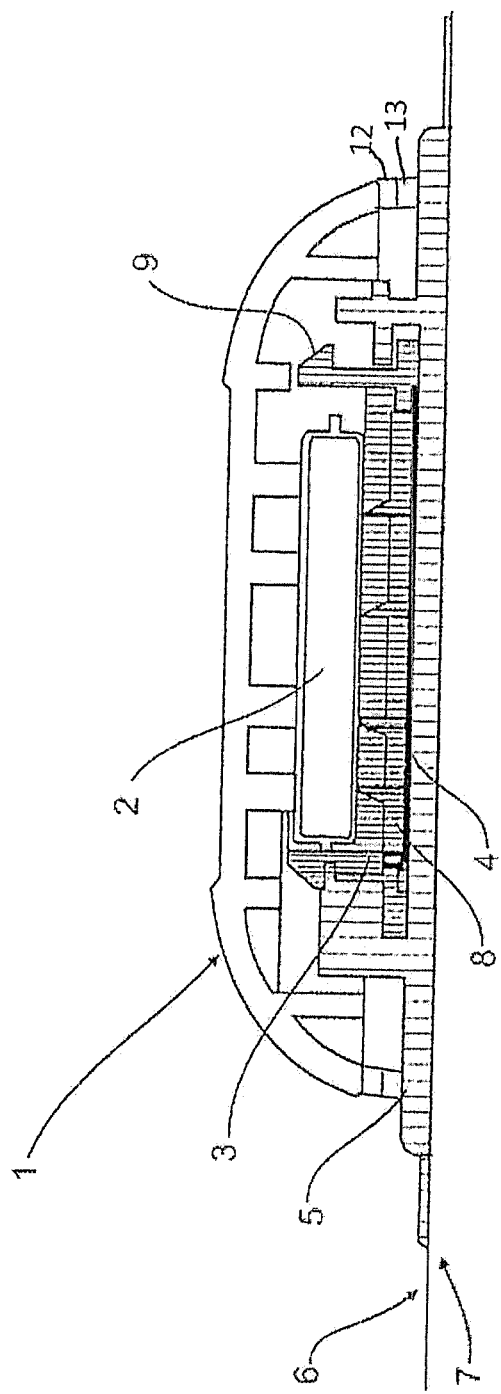
FIG. 2: shows the sectional view of the MNS in the storage position.
Figure 3:
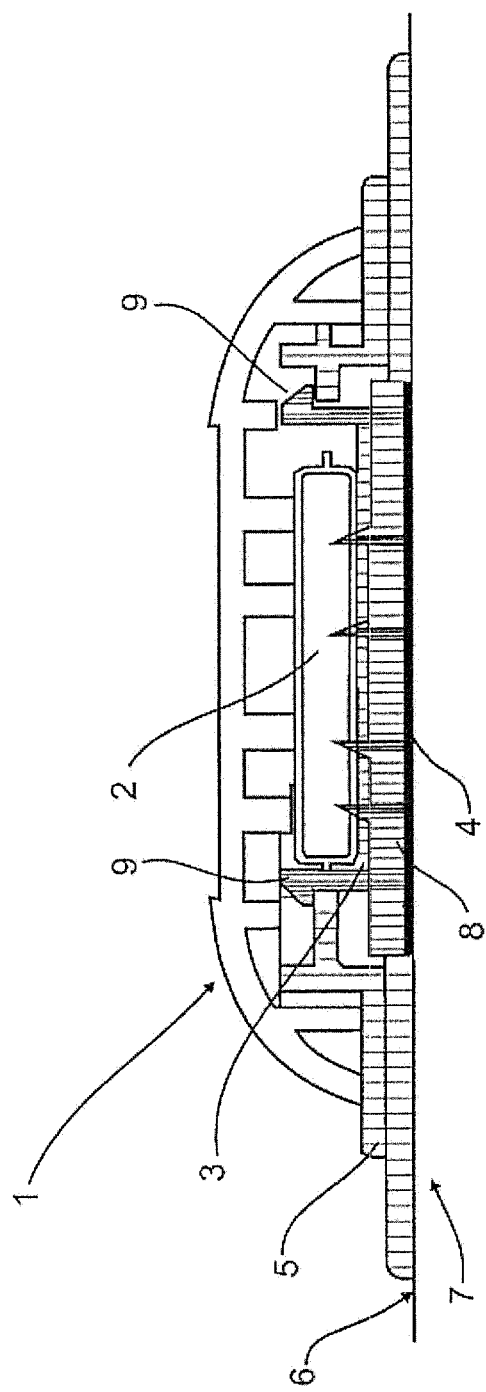
FIG. 3: shows the sectional view of the MNS in the delivery position.

Proceeding from the sectional view of the MNS in the storage position according to FIG. 2, first the protective film (7) is removed, and the MNS is fixed to the skin by way of the surgical tape (6). A quarter turn of the thread of the cap (3) about the base plate (5) causes the blow-fill-seal container, the frame (3) and the MNA (4) to be linearly displaced with respect to the base plate (5), and the active substance container (2) to be opened by mandrels (opening elements (8)) on the base plate (5).

KEY (1) cover element
(2) active substance container
(3) frame
(4) microneedle array
(5) base plate
(6) surgical tape
(7) protective film
(8) opening elements
(9) catch hooks
(10) base plate recesses
(11) cover element markings
(12) cover element thread
(13) base plate thread
(14) peripheral projection
(15) base plate opening
(16) base plate edge
(17) outer side
(18) tape recess

The invention claimed is:

1. A microneedle system for intradermal delivery, comprising: a base plate, the base plate being at least partially joined to a surgical tape, a frame directly above and movably connected to the base plate, a microneedle array in the frame for joint movement with the frame, an active substance container accommodated in the frame directly above the microneedle array and the base plate, the base plate having opening for receiving the microneedle array when the frame is linearly displaced in the direction of the opening in the base plate whereby the microneedle array may penetrate the skin of a patient, the base plate having at least one opening element for opening the active substance container to permit a substance to flow from the active substance container, the at least one opening element being separate and distinct from the microneedle array, the surgical tape having at least one passageway for permitting the substance from the active substance container to reach the skin of the patient, a cover element directly over the active substance container, the cover element being movably connected to the base plate by a thread on the cover element engaged with a complementary thread on the base plate, the microneedle system being activated from a cover element storage position of the cover element and an active substance container storage position of the active storage container to a cover element delivery position of the cover element and an active substance container delivery position of the active substance container by rotation of the cover element to move the cover element closer to the base plate and cause the at least one opening element to open the active substance container and to lower the microneedle array into contact with the skin, and the cover element being in contact with the frame to push the frame in the direction of the opening in the base plate when the microneedle system moves from the cover element storage position to the cover element delivery position and to also move the entire active substance container along with the frame from the active substance container storage position to the active substance container delivery position, and the cover element being more tightly in threaded engagement with the base plate in the cover element delivery position than in the cover element storage position, wherein the base plate has a peripheral projection extending upwardly around the periphery of the base plate opening, the base plate having an edge, the peripheral projection being inwardly offset with respect to the base plate edge, the at least one opening element being on an inner surface of the peripheral projection, and the base plate complementary thread being on an outer side of the edge.

2. The microneedle system according to claim 1, wherein the frame comprises one or more catch hooks engaged in recesses in the base plate.

3. A microneedle system for intradermal delivery, comprising: a base plate, the base plate being at least partially joined to a surgical tape, a frame directly above and movably connected to the base plate, a microneedle array in the frame for joint movement with the frame, an active substance container accommodated in the frame directly above the microneedle array and the base plate, the base plate having opening for receiving the microneedle array when the frame is linearly displaced in the direction of the opening in the base plate whereby the microneedle array may penetrate the skin of a patient, the base plate having at least one opening element for opening the active substance container to permit a substance to flow from the active substance container, the at least one opening element being separate and distinct from the microneedle array, the surgical tape having at least one passageway for permitting the substance from the active substance container to reach the skin of the patient, a cover element directly over the active substance container, the cover element being movably connected to the base plate by a thread on the cover element engaged with a complementary thread on the base plate, the microneedle system being activated from a cover element storage position of the cover element and an active substance container storage position of the active storage container to a cover element delivery position of the cover element and an active substance container delivery position of the active substance container by rotation of the cover element to move the cover element closer to the base plate and cause the at least one opening element to open the active substance container and to lower the microneedle array into contact with the skin, and the cover element being in contact with the frame to push the frame in the direction of the opening in the base plate when the microneedle system moves from the cover element storage position to the cover element delivery position and to also move the entire active substance container along with the frame from the active substance container storage position to the active substance container delivery position, and the cover element being more tightly in threaded engagement with the base plate in the cover element delivery position than in the cover element storage position, wherein the frame comprises one or more catch hooks engaged in recesses in the base plate, wherein the one or more catch hooks prevent rotation of the frame within the base plate, and the cover element being in contact with the frame by being in contact with the one or more catch hooks.

4. The microneedle system according to claim 3, wherein the thread on the cover element thread is located on a bottom side of the cover element and comprises a peripheral thread.

5. The microneedle system according to claim 3, wherein the cover element comprises one or more markings, which define how the microneedle system can be transferred from the storage position into the delivery position.

6. The microneedle system according to claim 3, wherein the surgical tape is protected by a protective film.

7. The microneedle system according to claim 3, wherein the diameter of the microneedle system is at least 10 mm.

8. The microneedle system according to claim 3, wherein the diameter of the microneedle system is at least 25 mm.

9. The microneedle system according to claim 3, wherein the diameter of the microneedle system is at least 50 mm.

10. The microneedle system according to claim 3, wherein the height of the microneedle system is no more than 30 mm.

11. The microneedle system according to claim 3, wherein the height of the microneedle system is no more than 20 mm.

12. The microneedle system according to claim 3, wherein the height of the microneedle system is no more than 10 mm.

13. The microneedle system according to claim 9, wherein the height of the microneedle system is no more than 10 mm.

14. The microneedle system according to claim 3, wherein the active substance container is a blow-fill-seal container or a disposable container.

15. The microneedle system according to claim 3, wherein the active substance container contains one or more substances, medicinal drugs, active agents, solutions or liquid formulations.

16. The microneedle system according to claim 3, comprising the active substance container, containing active substances in a liquid formulation for use in the intradermal delivery.

17. The microneedle system according to claim 3, wherein the entire active substance container is spaced from and out of contact with the cover element.

18. The microneedle system according to claim 3, wherein the at least one opening element and the microneedle array are positioned for making simultaneous contact with the substance container and the skin respectively.

* * * * *